United States Patent [19]

Martinez Roldan et al.

[11] 3,951,995

[45] Apr. 20, 1976

[54] METHOD FOR INDUSTRIAL PRODUCTION OF N-SUBSTITUTED DIPROPYLACETAMIDES

[75] Inventors: Christobal Martinez Roldan; Miguel Fernandez Braña; Jose Maria Castellano Berlanga, all of Madrid, Spain

[73] Assignee: Laboratorios Made, S.A., Madrid, Spain

[22] Filed: Oct. 24, 1974

[21] Appl. No.: 517,550

[30] Foreign Application Priority Data
Oct. 30, 1973  Spain .................................. 420074

[52] U.S. Cl. .................. 260/295 AM; 260/295.5 A; 424/263; 424/266
[51] Int. Cl.² ....................................... C07D 213/56
[58] Field of Search .............. 260/295 AM, 295.5 A

[56] References Cited
UNITED STATES PATENTS 3,324,179  6/1967  Scholz et al. ................ 260/295 AM
3,367,940  2/1968  Hotten ......................... 260/295 AM
3,822,276  7/1974  Meisels et al. ............... 260/295 AM

OTHER PUBLICATIONS

Klingsberg, Pyridine and its Derivatives, Part III, p. 218–219.

Primary Examiner—Norman A. Drezin
Attorney, Agent, or Firm—Woodhams, Blanchard and Flynn

[57] ABSTRACT

Compounds having the formula

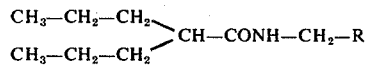

wherein R is 2-picolyl, 3-picolyl or 4-picolyl. The compounds are prepared by reacting dipropylacetic acid, or the corresponding chloride or anhydride, with 2-picolylamine, 3-picolylamine or 4-picolylamine. The compounds possess anti-convulsant and barbiturate potentiation properties.

4 Claims, No Drawings

METHOD FOR INDUSTRIAL PRODUCTION OF N-SUBSTITUTED DIPROPYLACETAMIDES

The present invention relates to N-substituted dipropylacetamides which show remarkable anti-convulsant and barbiturate potentiation properties. These compounds have the following formula:

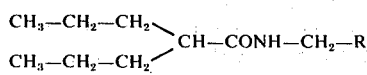

wherein R is 2-picolyl, 3-picolyl or 4-picolyl. The method of synthesis of these compounds is based on the reaction of activated derivatives of the acid, such as halides or acid anhydrides thereof, with the corresponding amine, either directly or in presence of an organic or inorganic base, recovering the obtained salt as such by means of a direct reaction or treating same with a base of similar characteristics as the aforementioned in order to free the compound, and purifying the obtained products by crystallization in a suitable solvent.

EXAMPLE No. 1

Into a 100 ml flask having two openings, provided with an electromagnetic agitator, reflux refrigerant with calcium chloride tube and a funnel with tap, there is placed 5.1 g (0.03 mole) of dipropylacetyl chloride dissolved in 20 ml of dry benzene. To this solution there is added through the funnel, dropwise and with agitation, 3.4 g (0.03 mole) of 2-picolylamine, dissolved in 10 ml of dry benzene. The reaction is exothermic and during the addition a precipitation takes place. Once this precipitation is finished the agitation is maintained for 2 hours after which the formed solid is filtered and dissolved in water. The aqueous solution is alkalized in 10% caustic soda and an oil forms which coagulates upon cooling. The formed solid is filtered and it is crystallized with cyclohexane. The N-(2-picolyl)-dipropylacetamide is a white solid of m.p. = 84°–86° C (without correction).

Analysis: Calculated for $C_{14}H_{22}N_2O$: C: 71.75; H: 9.46; N: 11.95. Found: C: 71.32; H: 9.61; N: 12.27.

EXAMPLE NO. 2

Into a 100 ml flask having two openings, provided with an electromagnetic agitator, reflux refrigerant with calcium chloride tube and a funnel with tap, there is placed 5.1 g (0.03 mole) of dipropylacetyl chloride dissolved in 20 ml of dry benzene. To this solution there is added through the funnel, dropwise and with agitation, 3.4 g (0.03 mole) of 3-picolylamine dissolved in 10 ml of dry benzene. The reaction is exothermic and during the addition precipitation takes place. Once this precipitation is finished, agitation is maintained for 2 hours after which the formed solid is filtered and dissolved in water. The aqueous solution is alkalized in 10% caustic soda and an oil forms which coagulates upon cooling. The formed solid is filtered and crystallized with cyclohexane. The N-(3-picolyl)-dipropylacetamide is a white solid of m.p. = 64°–66° C (without correction)

Analysis: Calculated for $C_{14}H_{22}N_2O$: C: 71.75; H: 9.46; N: 11.95. Found: C: 71.79; H: 9.49 N: 12.17.

EXAMPLE NO. 3

Into a 100 ml flask having two openings, provided with an electromagnetic agitator, reflux refrigerant with calcium chloride tube and a funnel with tap, there is placed 5.1 g (0.03 mole) of dipropylacetyl chloride dissolved in 20 ml of dry benzene. To this solution there is added through the funnel, dropwise and with agitation, 3.4 g (0.03 mole) of 4-picolyl amine dissolved in 10 ml of dry benzene. The reaction is exothermic and during the addition a precipitation takes place. Once this precipitation is finished, shaking is maintained for 2 hours, after which the formed solid is filtered and dissolved in water. The aqueous solution is alkalized in 10% caustic soda and an oil forms which coagulates upon cooling. The formed solid is filtered and crystallized in water.

Analysis: Calculated for $C_{14}H_{22}N_2O$: C: 71.75; H: 9.46; N: 11.95. Found: C: 71.64; H: 9.46; N: 11.86.

EXAMPLE NO. 4

Into a 100 ml flask, provided with reflux refrigerant with calcium chloride tube, there is placed 1.0 g (0.01 mole) of 4-picolylamine, 2.6 g (0.01 mole) of dipropylacetic anhydride and 20 ml of dry chloroform and the mixture is boiled at on reflux for 1 hour; and then it is cooled. The mixture is washed with a 5% sodium bicarbonate solution, with water and finally dried with anhydrous magnesium sulfate. Once the solvent is eliminated, a solid will be obtained which, once crystallized, has physical constants in agreement with those of Example no. 3.

PROPERTIES OF THE COMPOUNDS

Compounds

I — N-(2-picolyl) - dipropylacetamide
II — N-(3-picolyl) - dipropylacetamide
III — N-(4-picolyl) - dipropylacetamide These three compounds have proved to have an antiepileptic activity. Diazepam has been used as a comparison drug.

1. Acute toxicity

The lethal dose 50 ($LD_{50}$) has been determined on albino rats I.C.R. Swiss, of both sexes, weighing 24 ± 2 g. The drugs have been administered by intraperitoneal way.

| Compound | $LD_{50}$ (mg/kg) | dilution vehicle |
|---|---|---|
| I | >1.600 | suspended in acacia gum |
| II | 95 | HCl |
| III | 264 | HCl |
| Diazepam | 270 | suspended in acacia gum |

2. Potentiation of barbiturates

Albino rats I.C.R. Swiss weighing 25 ± 2 g have been used. There have been made 5 lots of 20 rats per lot, which received sodium pentobarbital 60 mg/kg by intraperitoneal way, 30 minutes after the administration of compounds I, II, III and Diazepam in the test lots and distilled water in the control lot, according to the following schedule:

Lot (1): Sodium pentobarbital 60 mg/kg + I (180 mg/kg).

Lot (2): Sodium pentobarbital 60 mg/kg + II (35 mg/kg).

Lot (3): Sodium pentobarbital 60 mg/kg + III (18 mg/kg).
Lot (4): Sodium pentobarbital 60 mg/kg + Diazepam (3,6 mg/kg).
Lot (5): Sodium pentobarbital 60 mg/kg + distilled $H_2O$ (control lot).

The number of animals awake after 180 minutes after the administration of the barbiturate are noted. The following results have been obtained according to the statistic test of $Chi^2$:

| Treatment | Awake after 180 minutes | Asleep | Total |
|---|---|---|---|
| Control | 19 | 1 | 20 |
| Lot 1 | 3 | 17 | 20 |
| | $p<0.001$ | | |

The compound I potentiates clearly the hypnotic effect of the pentobarbital.

| Treatment | Awake after 180 minutes | Asleep | Total |
|---|---|---|---|
| Control | 19 | 1 | 20 |
| Lot 2 | 6 | 14 | 20 |
| | $p<0.001$ | | |

The compound II potentiates clearly the hypnotic effect of the pentobarbital.

| Treatment | Awake after 180 minutes | Asleep | Total |
|---|---|---|---|
| Control | 16 | 4 | 20 |
| Lot 3 | 1 | 19 | 20 |
| | $p<0.001$ | | |

The compound III potentiates clearly the hypnotic effect of the pentobarbital.

| Treatment | Awake after 180 minutes | Asleep | Total |
|---|---|---|---|
| Control | 16 | 4 | 20 |
| Lot 4 | 5 | 15 | 20 |

| Treatment | Awake after 180 minutes | Asleep | Total |
|---|---|---|---|
| | $p<0.02$ | | |

Diazepam potentiates clearly the hypnotic effect of pentobarbital, but not as much as the three compounds according to this invention.

3. Anti-convulsant activity

There have been made anti-convulsant tests on albino rats I.C.R. Swiss with strychnine and 3-methyl-3-ethylglutarimide (bemegride), employing the three compounds and Diazepam. Results have been positive with cardiazol. There have been employed 4 lots of 10 rats per lot, which received:

Lot (1): I 180 mg/kg and after 30 minutes cardiazol 1 mg/rat.
Lot (2): II 35 mg/kg and after 30 minutes cardiazol 1 mg/rat.
Lot (3): III 18 mg/kg and after 30 minutes cardiazol 1 mg/rat.
Lot (4): Diazepam 3,6 mg/kg and after 30 minutes cardiazol 1 mg/rat.

Each lot has been compared with a control lot which has received only cardiazol at the same dose as in the previous lots. The results obtained are the following:

| Treatment | number of animals with convulsions | number of dead animals |
|---|---|---|
| Lot 1 | 9 | 7 |
| control | 10 | 10 |

Compound I produces a protection of 30% of the lethal effect of the cardiazol.

| Treatment | number of animals with convulsions | number of dead animals |
|---|---|---|
| Lot 2 | 0 | 0 |
| Control | 10 | 10 |

Compound II produces a protection of 100% of the convulsions and of the lethal effect of the cardiazol.

| Treatment | number of animals with convulsions | number of dead animals |
|---|---|---|
| Lot 3 | 1 | 0 |
| Control | 5 | 0 |

Compound III produces a protection of 40% of the convulsion effect of cardiazol.

| Treatment | Number of animals with convulsions | number of dead animals |
|---|---|---|
| Lot 4 | 0 | 0 |
| Control | 8 | 0 |

The diazepam produces a 100% protection against the convulsions originated by cardiazol.

We claim:
1. A compound having the formula

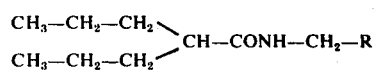

wherein R is 2-picolyl, 3-picolyl or 4-picolyl.

2. A compound as claimed in claim 1, in which R is 2-picolyl.

3. A compound as claimed in claim 1, in which R is 3-picolyl.

4. A compound as claimed in claim 1, in which R is 4-picolyl.

* * * * *